(12) United States Patent
Sundaram et al.

(10) Patent No.: US 9,028,595 B2
(45) Date of Patent: May 12, 2015

(54) KINETIC FRACTIONATORS, AND CYCLING PROCESSES FOR FRACTIONATION OF GAS MIXTURES

(71) Applicants: Narasimhan Sundaram, Annandale, NJ (US); P. Scott Northrop, Spring, TX (US)

(72) Inventors: Narasimhan Sundaram, Annandale, NJ (US); P. Scott Northrop, Spring, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 0 days.

(21) Appl. No.: 14/554,901

(22) Filed: Nov. 26, 2014

(65) Prior Publication Data

US 2015/0082986 A1 Mar. 26, 2015

Related U.S. Application Data

(62) Division of application No. 13/877,315, filed as application No. PCT/US2011/053275 on Sep. 26, 2011, now Pat. No. 8,921,637.

(60) Provisional application No. 61/413,845, filed on Nov. 15, 2010.

(51) Int. Cl.
*B01D 53/04* (2006.01)
*B01D 53/047* (2006.01)

(52) U.S. Cl.
CPC ........ *B01D 53/0407* (2013.01); *B01D 53/0446* (2013.01); *B01D 53/047* (2013.01); *B01D 2256/245* (2013.01); *B01D 2257/304* (2013.01); *B01D 2257/504* (2013.01)

(58) Field of Classification Search
None
See application file for complete search history.

(56) References Cited

U.S. PATENT DOCUMENTS

| | | | |
|---|---|---|---|
| 7,169,213 B2* | 1/2007 | Liu et al. | 96/4 |
| 7,938,886 B2* | 5/2011 | Hershkowitz et al. | 95/115 |
| 2006/0090651 A1* | 5/2006 | Liu et al. | 96/121 |
| 2011/0031173 A1* | 2/2011 | Kent | 210/130 |
| 2014/0208797 A1* | 7/2014 | Kelley et al. | 62/611 |

\* cited by examiner

*Primary Examiner* — Tam M Nguyen
(74) *Attorney, Agent, or Firm* — ExxonMobil Upstream Research Company Law Department (57) ABSTRACT

A process for separating methane from a natural gas mixture employs pressure swing adsorption in one or more vessels. Each vessel has an adsorbent material having a kinetic selectivity for contaminants over methane greater than 5. Contaminants within the natural gas mixture become gases kinetically adsorbed within the adsorbent material. The vessel is placed under pressure to cause contaminants to be adsorbed in the surfaces and micro-pores of the adsorbent material. The process includes releasing a product stream comprised at least 95% by volume methane from a first gas outlet in the vessel, and desorbing the contaminant gases from the adsorbent material by reducing the pressure within the vessel. The desorbing step is done without applying heat to the vessel, thereby delivering a waste gas stream comprised at least 95% by volume of the contaminant gases. An improved fractionation vessel having both major and minor flow channels is also provided.

14 Claims, 6 Drawing Sheets

510 — Direct a Natural Gas Mixture into a Gas Separation Unit, the Gas Separation Unit Having at Least One Vessel Having an Adsorbent Material 520 — Place the at Least One Vessel Under Pressure to Cause Contaminants to be Adsorbed to the Adsorbent Material 530 — Release a Product Stream Comprised at Least 95% by Volume of Methane From a First Gas Outlet 540 — Desorb the Contaminant Gases from the Adsorbent Material by Reducing the Pressure Within the at Least One Vessel Without Applying Heat to the Vessel, Thereby Delivering a Waste Gas Stream Comprised at least 95% by Volume of the Contaminant Gases 550 — Optionally, Select an Ionic Fluid as an Absorbent to Enhance Adsorptive Properties of the Adsorbent Material 560 — Place the Selected Ionic Fluid Onto Stepped Surfaces Before Directing the Natual Gas Mixture into a Gas Inlet 570 — Apply a Magnetic Field to the Ferromagnetic Adsorbent Material in the at Least One Vessel

KINETIC FRACTIONATORS, AND CYCLING PROCESSES FOR FRACTIONATION OF GAS MIXTURES

CROSS REFERENCE TO RELATED APPLICATIONS

This application is a divisional of U.S. patent application Ser. No. 13/877,315 now U.S. Pat. No. 8,921,637 that published as U.S. Patent Publication No. 2013/0225898, which is the National Stage entry under 35 U.S.C. 371 of Intl. Patent Application PCT/US2011/053275 that published as Intl. Patent App. Pub. No. 2012/067719 and claims the benefit of and priority from U.S. Provisional Patent Application 61/413,845, filed Nov. 15, 2010, entitled KINETIC FRACTIONATORS, AND CYCLING PROCESSES FOR FRACTIONATION OF GAS MIXTURES, the entirety of which are each incorporated by reference herein, for all purposes.

This application is related to U.S. patent application Ser. No. 12/080,783, which was filed on Apr. 4, 2008 and published as U.S. Pat. Publ. No. 2008/0282887. That application is titled "Removal of $CO_2$, $N_2$, and $H_2S$ from Gas Mixtures Containing Same," and is incorporated herein by reference in its entirety. That application, in turn, claimed the benefit of U.S. Prov. Pat. Appl. No. 60/930,826 filed May 18, 2007.

BACKGROUND

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

FIELD OF THE INVENTION

The present invention relates to the field of fluid separation. More specifically, the present invention relates to the separation of carbon dioxide and other acid gases from a hydrocarbon fluid stream.

DISCUSSION OF TECHNOLOGY

The production of hydrocarbons from a reservoir oftentimes carries with it the incidental production of non-hydrocarbon gases. Such gases include contaminants such as carbon dioxide ($CO_2$), hydrogen sulfide ($H_2S$), and mercaptans. When such contaminants are produced as part of a hydrocarbon gas stream, the gas stream may be referred to as "sour gas." Further, the $CO_2$, $H_2S$, and mercaptans components within the sour gas may be referred to, separately or together, as "acid gas."

It is desirable to separate out the acid gas components at a gas processing facility. This can be accomplished by first removing a substantial portion of the water from the raw gas stream. Water is typically removed by chemically mixing glycol into the raw gas stream to cause the water to break out of solution. The water and glycol are then captured through a bottom aqueous stream. A separate dehydrated gas stream is released.

The dehydrated gas stream is a sour gas stream, with the sour gas components remaining after dehydration. Therefore, further gas separation processes are applied. In some instances where the carbon dioxide component is particularly high, the sour gas may also be taken through a Joule-Thompson valve for flash cooling, and then carried into a cryogenic distillation tower or bulk fractionation unit for the removal of $CO_2$.

In other instances, particularly where the $H_2S$ component or heavy hydrocarbon components are higher, the sour gas steam may be flowed across an adsorbent bed. Adsorbent beds operate on the principle that different molecules can have different affinities for adsorption. This provides a mechanism for the adsorbent to discriminate between different gasses.

Different types of adsorbent beds are known. Typical adsorbents include activated carbons, silica gels, aluminas, and zeolites. In some cases, a polymeric material can be used as the adsorbent material. In any instance, the adsorbent bed preferentially adsorbs a more readily adsorbed component (known as the "heavy" gas) relative to a less readily adsorbed component (known as the "light" gas) of the gas mixture.

In order to effectuate the separation, adsorbent beds employ a highly porous microstructure. Gas molecules become attached to the surface area provided along the pores. The gas adsorbed on the interior surfaces of the micro-porous material may consist of a layer only one, or at most a few, molecules thick; however, surface areas of several hundred square meters per gram enable the adsorption of a significant portion of the adsorbent's weight in gas. Thus, adsorbent beds may be beneficially used for component separation.

In addition to their affinity for different gases, zeolites and some types of activated carbons, called carbon molecular sieves, may utilize their molecular sieve characteristics to exclude or slow the diffusion of some gas molecules into their structure. This provides a mechanism for selective adsorption based on the size of the molecules. In this instance, the adsorbent bed restricts the ability of larger molecules to be adsorbed, thus allowing the gas to selectively fill the micro-porous structure of an adsorbent material with one or more species from a multi-component gas mixture.

In some instances, the gas stream is not dehydrated before being passed across an adsorbent bed. Some adsorbent beds will preferentially bond with water molecules along with other contaminants, and allow methane and inert gas components such as hydrogen and nitrogen to pass. However, the presence of water can make a later desorption stage (known as "regeneration") more challenging. In this respect, as the micro-pores of an adsorbent bed become filled with molecular contaminants, the bed must be taken out of service and de-pressurized. When there is a significant presence of water, removal of water may require heating.

Different adsorption techniques for gas separation are known. One adsorption technique is pressure swing adsorption, or "PSA." PSA processes rely on the fact that, under pressure, gaseous contaminants tend to be adsorbed within the pore structure of an adsorbent material, or within the free volume of a polymeric material, to different extents. The higher the pressure in the adsorption vessel, the more gas is adsorbed. In the case of natural gas, the natural gas mixture may be passed under pressure through an adsorption vessel. The pores of the polymeric or micro-porous adsorbent become filled with hydrogen sulfide and carbon dioxide to a greater extent than with methane. Thus, most or even all of the $H_2S$ and $CO_2$ will stay in the sorbent bed, while the gas coming out of the vessel will be enriched in methane. Any remaining water and any heavy hydrocarbons (such as ethane) will also be retained. In addition, any benzene, toluene, or other volatile organic compounds will be retained.

When the adsorbent bed reaches the end of its capacity to adsorb contaminants, it can be regenerated by reducing the pressure. This causes the vessel to release the adsorbed components. A concentrated contaminant stream is thus released separate from the methane stream. In this way, the adsorption bed may be regenerated for subsequent re-use.

In most PSA cases, reducing the pressure in the pressurized chamber down to ambient pressure will cause a majority of the hydrogen sulfide and other contaminants to be released from the adsorbent bed. In some cases, the pressure swing adsorption system may be aided by the use of a vacuum chamber to apply sub-ambient pressure to the concentrated contaminant stream. In the presence of lower pressure, sulfurous components, carbon dioxide, and heavy hydrocarbons will more completely desorb from the solid matrix making up the adsorbent bed.

A related gas separation technique is temperature swing adsorption, or "TSA." TSA processes also rely on the fact that gases tend to be adsorbed within the pore structure of microporous adsorbent materials or within the free volume of a polymeric material, to different extents. When the temperature of the adsorbent bed in the vessel is increased, the adsorbed gas molecules are released, or de-sorbed. By cyclically swinging the temperature of adsorbent beds within a vessel, TSA processes can be used to separate gases in a mixture.

A combination of thermal swing regeneration and pressure swing regeneration may be employed. In either instance, the released methane-enriched gas may be taken through a subsequent refrigeration unit, if necessary, to bring the $CO_2$ composition down to pipeline or LNG specifications. This allows any remaining $CO_2$ to liquefy and be removed as a liquid acid gas stream. Still further cooling energy may be optionally applied to generate liquefied natural gas, or LNG.

An adsorbent bed system may rely on a plurality of beds in parallel. These beds may be packed, for example, with activated carbons or molecular sieves. A first bed is used for adsorption. This is known as a service bed. A second bed undergoes regeneration, such as through pressure reduction while the first bed is in service. Yet a third bed has already been regenerated and is held in reserve for use in the adsorption system when the first bed becomes substantially saturated. Thus, a minimum of three beds may be used in parallel for a more efficient operation.

The pressure swing adsorption system may be a rapid cycle pressure swing adsorption system. In the so-called "rapid cycle" processes, cycle times can be as small as a few seconds. A rapid cycle PSA ("RCPSA") unit can be particularly advantageous, as such units are quite compact relative to normal PSA devices. Further, RCPSA contactors can enable a significant increase in process intensification (e.g., higher operating frequencies and gas flow velocities) when compared to conventional PSA.

Existing PSA and RCPSA processes rely heavily on equilibrium separation or on thermal swing operation. These operations lead to larger cycle times and larger equipment footprints. Therefore, a need exists for a process that employs pressure swing adsorption to obtain high purity production separation without the need for heating of the adsorption vessel or thermal swing operation.

SUMMARY

Processes for separating methane from a natural gas mixture are provided herein. The processes employ pressure swing adsorption in one or more vessels. Each vessel has an adsorbent material having a kinetic selectivity for contaminants over methane that has a value greater than 5. In this way, contaminants within the natural gas mixture become gases kinetically adsorbed within the adsorbent material. The contaminants may be $CO_2$, $H_2S$, $H_2O$, heavy hydrocarbons, VOC's, or combinations thereof.

Each vessel has a gas inlet and a first gas outlet. In addition, each vessel has at least two major flow channels through the adsorbent material. The major flow channels place the gas inlet and the first gas outlet in fluid communication.

In accordance with the process, the process also includes directing the natural gas mixture into a gas separation unit. The process further includes placing the at least one vessel under pressure to cause contaminants in the natural gas mixture to be adsorbed onto the adsorbent material. The contaminants reside under pressure in the surfaces and micro-pores of the adsorbent material.

The process then includes releasing a product stream comprised at least 95% by volume of methane. The product stream is released from a first gas outlet in the vessel. The product stream may further comprise hydrogen, nitrogen, or combinations thereof. The process also includes desorbing the contaminant gases from the adsorbent material by reducing the pressure within the vessel. The desorbing step is done without applying heat to the vessel. A waste gas stream is thereby delivered that comprises at least 95% by volume of the contaminant gases.

Preferably, the releasing and desorbing steps take place in a combined cycle of less than one minute.

The waste gas stream from the desorbing step may be delivered through the gas inlet. Alternatively, valving may be arranged so that the waste gas stream is delivered through the gas outlet. In one aspect, the at least one adsorbent vessel further comprises a second gas outlet intermediate the gas inlet and the first gas outlet. In this instance, desorbing the contaminant gases releases a first portion of the waste gas stream from the first gas outlet, and a second portion of the waste gas stream from the second gas outlet.

Additionally or alternatively, in some implementations, the step of desorbing the contaminant gases comprises releasing a first portion of the waste gas stream during a first time period, and a second portion of the waste gas stream during a second time period. The first portion of the waste gas stream may comprise at least 98% by volume $CO_2$; the second portion of the waste gas stream may comprise nitrogen, hydrogen, methane, $H_2O$, or combinations thereof. Thus, the first and second waste gas stream portions may have different compositions.

Fractionation vessels for separating methane from a natural gas mixture are also provided herein. In some embodiments, the vessel includes a housing. The vessels also include a gas inlet for receiving the natural gas mixture into the housing, and a first gas outlet for releasing at least a portion of the natural gas mixture from the housing. The gas inlet is capable of receiving the natural gas mixture into the housing at a pressure of at least 100 psig.

The vessel further includes an adsorbent material within the housing. The adsorbent material has a kinetic selectivity for contaminants over methane greater than 5. In this way, the contaminants become kinetically adsorbed within the adsorbent material in gas phase.

The vessel also includes at least two major flow channels through the adsorbent material. The major flow channels place the gas inlet and the first gas outlet in fluid communication. The vessel further includes at least one minor flow channel through the adsorbent material. The minor channel is in fluid communication with the major channels.

In one aspect, the fractionation vessel also has a second gas outlet. The second gas outlet is intermediate the gas inlet and the first gas outlet. The second gas outlet release a portion of a waste gas stream when the vessel is desorbed.

In some implementations, the at least two major flow channels is formed from and along the major axis of a plurality of rods. Further, the plurality of rods are spaced substantially equi-distantly apart, providing the flow channels with a substantially uniform volume.

In one aspect, the at least two minor flow channels is formed by a plurality of stepped surfaces along the respective rods. In another aspect, the at least two minor flow channels is formed by flow channels that intersect the at least two major flow channels and which place the gas inlet and the second gas outlet in fluid communication.

BRIEF DESCRIPTION OF THE DRAWINGS

So that the present inventions can be better understood, certain drawings, charts, graphs and/or flow charts are appended hereto. It is to be noted, however, that the drawings illustrate only selected embodiments of the inventions and are therefore not to be considered limiting of scope, for the inventions may admit to other equally effective embodiments and applications.

FIG. 2B provides an exploded view of the adsorbent bed of FIG. 2A.

DETAILED DESCRIPTION OF CERTAIN EMBODIMENTS

Definitions

As used herein, the term "hydrocarbon" refers to an organic compound that includes primarily, if not exclusively, the elements hydrogen and carbon. Hydrocarbons generally fall into two classes: aliphatic, or straight chain hydrocarbons, and cyclic, or closed ring, hydrocarbons including cyclic terpenes. Examples of hydrocarbon-containing materials include any form of natural gas, oil, coal, and bitumen that can be used as a fuel or upgraded into a fuel.

As used herein, the term "hydrocarbon fluids" refers to a hydrocarbon or mixtures of hydrocarbons that are gases or liquids. For example, hydrocarbon fluids may include a hydrocarbon or mixtures of hydrocarbons that are gases or liquids at formation conditions, at processing conditions, or at ambient conditions (15° C. and 1 atm pressure). Hydrocarbon fluids may include, for example, oil, natural gas, coal bed methane, shale oil, pyrolysis oil, pyrolysis gas, a pyrolysis product of coal, and other hydrocarbons that are in a gaseous or liquid state.

As used herein, the term "fluid" refers to gases, liquids, and combinations of gases and liquids, as well as to combinations of gases and solids, combinations of liquids and solids, and combinations of gases, liquids, and solids.

As used herein, the term "condensable hydrocarbons" means those hydrocarbons that condense at about 15° C. and one atmosphere absolute pressure. Condensable hydrocarbons may include, for example, a mixture of hydrocarbons having carbon numbers greater than 4.

As used herein, the term "subsurface" refers to geologic strata occurring below the earth's surface.

As used herein, the term "pressure swing adsorption" shall be taken to include any one or more of the processes that employ a change in pressure for a purge cycle (e.g., PSA, PPSA, RCPSA, and RCPPSA).

As used herein, the term "wellbore" refers to a hole in the subsurface made by drilling or insertion of a conduit into the subsurface. A wellbore may have a substantially circular cross section, or other cross-sectional shapes. As used herein, the term "well," when referring to an opening in the formation, may be used interchangeably with the term "wellbore."

Description of Selected Specific Embodiments

The inventions are described herein in connection with certain specific embodiments. However, to the extent that the following detailed description is specific to a particular embodiment or a particular use, such is intended to be illustrative only and is not to be construed as limiting the scope of the inventions.

The present inventions are directed to novel pressure swing adsorption processes for the removal of undesirable gas components from a hydrocarbon gas stream. Such components include, for example, $CO_2$, $H_2S$, $H_2O$, heavy hydrocarbons, VOC's, mercaptans, or combinations thereof. The components represent contaminants in a natural gas mixture.

Figure 1:
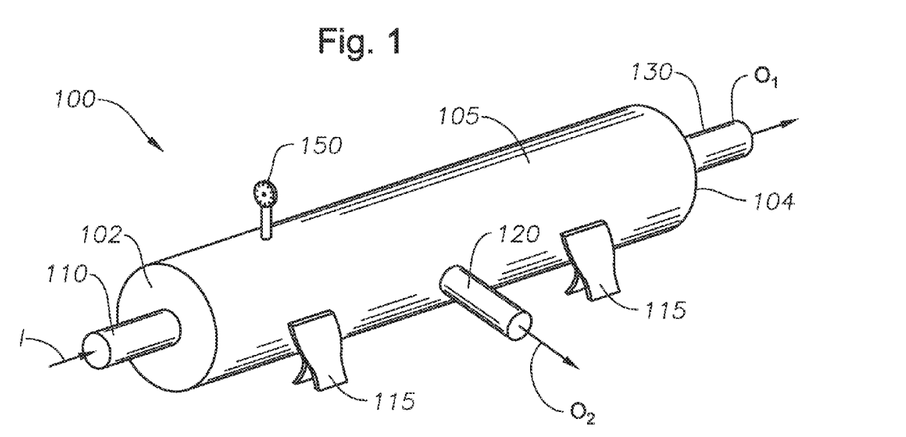
FIG. 1 is a perspective view of a pressure swing adsorption vessel as may be used in the processes of the present inventions. The vessel also represents a kinetic fractionator of the present inventions.

The processes of the present invention can better be understood with reference to the figures hereof. First, FIG. 1 is a perspective view of a pressure swing adsorption vessel 100. The vessel 100 is a contactor vessel, or "contactor," that operates for the purpose of receiving a natural gas mixture, and separating the mixture into at least two substantially pure components. One of those components is $CH_4$, or methane.

The composition of natural gas streams from a subsurface reservoir (raw natural gas) will vary from field to field. Non-limiting examples of components that may comprise a raw natural gas stream include water, condensates (higher molecular weight organics), methane, ethane, propane, butane, $CO_2$, $N_2$, He, $H_2S$, Hg, and mercaptans. Water and condensates are typically removed before the natural gas is directed into the vessel 100, and the condensates are sent to a petroleum refinery.

The vessel 100 defines an elongated, pressure-containing body. The vessel 100 includes a housing 105. Preferably, the housing 105 is fabricated from iron or steel. In the arrangement of FIG. 1, the vessel 100 is illustrated in a substantially horizontal orientation. However, the vessel 100 may alternatively be operated in a vertical orientation. In either instance, the vessel 100 may include various supporting legs or pads 115.

The vessel 100 is able to operate at high pressures so as to accommodate the inlet pressures experienced with the processing of natural gas. For example, such inlet pressures may exceed 200 psig, and more frequently may be greater than about 1,000 psig, or even 3,000 psig. To monitor internal pressure, the vessel 100 includes gauges or other pressure-monitoring devices. A representative gauge is shown at 150 in FIG. 1. Of course, it is understood that modern pressure-monitoring devices operate primarily as digital systems that interact with valves, clocks, and operational control software.

The vessel 100 has a first end shown at 102, and a second end shown at 104. A gas inlet 110 is provided at the first end 102, while a first gas outlet 130 is provided at the second end 104. Optionally, a second gas outlet 120 is provided intermediate the first end 102 and the second end 104, or intermediate the gas inlet 110 and the first gas outlet 130.

In operation, the vessel 100 serves as a kinetic fractionator, or adsorbent contactor. A natural gas mixture, or Feed Stream, is introduced into the vessel 100 through the gas inlet 110. Arrow "I" indicates the flow of fluid into the vessel 100. The natural gas is contacted within the vessel 100 by an adsorbent bed (not shown in FIG. 1). The adsorbent bed uses kinetic adsorption to capture contaminants. At the same time, the adsorbent bed releases a natural gas Product Stream through the first gas outlet 130. In the present arrangement, the Product Stream comprises at least 95% by volume methane. Flow of the natural gas Product Stream from the vessel 100 is indicated at arrow $O_1$.

It is understood that the vessel 100 is part of a larger gas separation unit (not shown). The gas separation unit will include valving, vessels, and gauges as needed to carry out regeneration of the adsorbent bed and the capture of the separated gas components. Regeneration is done using pressure swing adsorption. More preferably, regeneration is carried out using rapid cycle PSA.

Figure 6A:
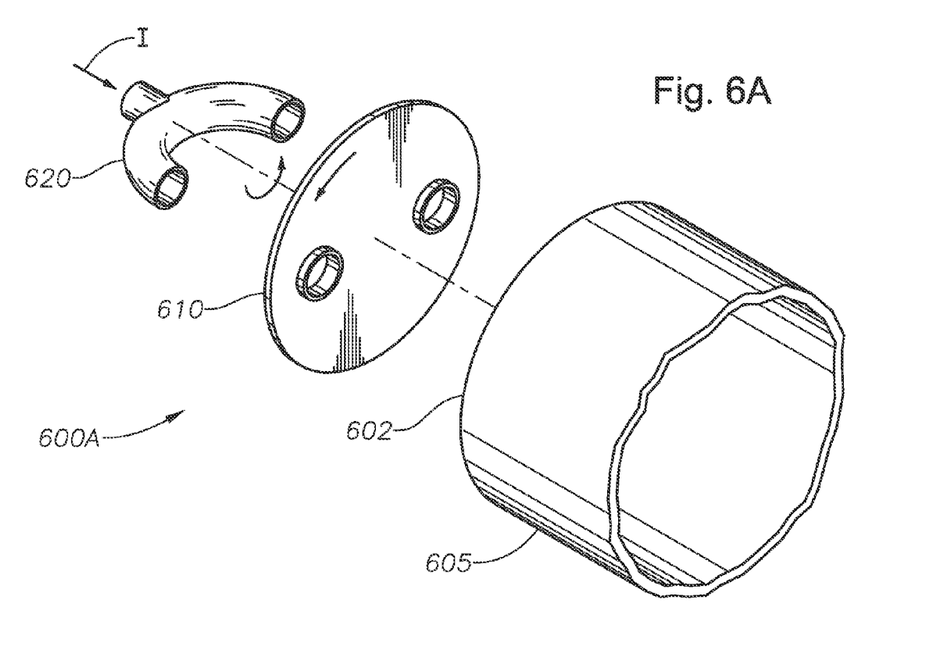
FIG. 6A is a portion of a pressure swing adsorption vessel as may be used in the processes of the present inventions. Here, rotary valving is provided for rapidly cycling a natural gas mixture.

FIG. 6A shows a portion of a pressure swing adsorption vessel 600A as may be used in the processes of the present inventions, for rapid cycle PSA. Here, rotary valving is provided for rapidly cycling a natural gas mixture. A natural gas mixture is shown entering the vessel 600A at arrow I.

The valving first includes a rotating manifold 610. The manifold rotates proximate a first end 602 of the vessel 600A. The valving also includes inlet flow channels 620. Here, the inlet flow channels 620 rotate relative to the manifold 610.

Figure 6B:
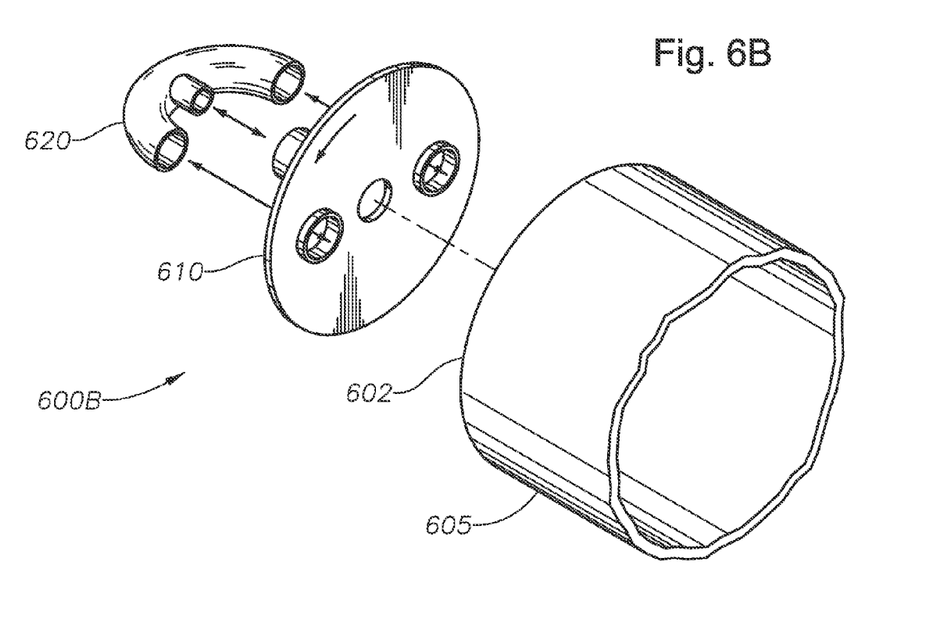
FIG. 6B shows a portion of a pressure swing adsorption vessel as may be used in the processes of the present inventions. Here, non-rotary valving is provided in addition to rotary valving for rapidly cycling a natural gas mixture.

FIG. 6B shows a portion of a second pressure swing adsorption vessel 600B as may be used in the processes of the present inventions, for rapid cycle PSA. Here, non-rotary valving is provided along with rotary valving for rapidly cycling of a natural gas mixture.

The valving again includes a rotating manifold 610. The manifold rotates proximate a first end 602 of the vessel 600B. The valving also includes inlet flow channels 620. Here, the inlet flow channels 620 reciprocate relative to the manifold 610.

The valving interfaces shown in FIGS. 6A and 6B are illustrative. It is understood that various combinations of rotating and non-rotating pipes and manifolds may be employed. Further, the valving may be extended to apply to multiple vessel manifolds to perform a complete cycle.

Figure 2A:
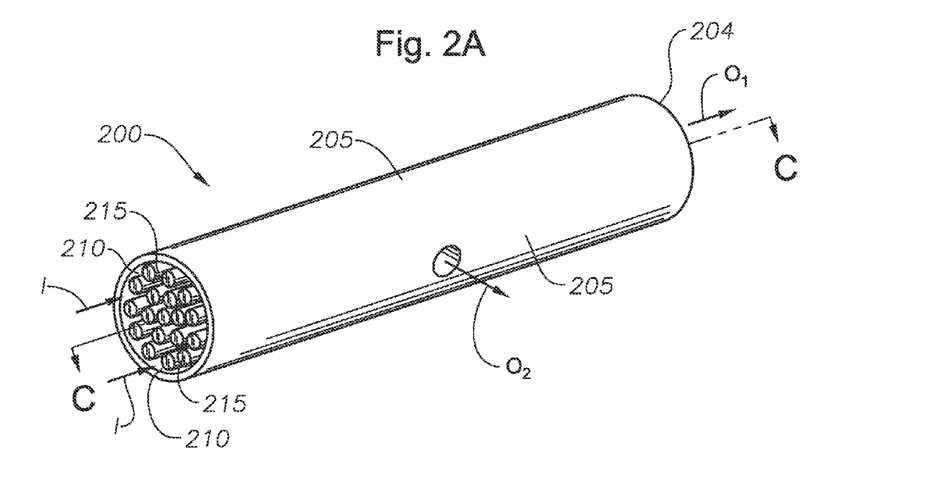
FIG. 2A is a perspective view of the adsorbent bed and flow channels for the pressure swing adsorption vessel of FIG. 1. Major flow channels are seen between adsorbent rods along a major axis of the adsorbent bed.

The vessel 100 and the vessels 600A, 600B utilize an adsorbent bed to capture contaminants on the surface of a micro-porous adsorbent material and along the pore spaces therein. FIG. 2A is a perspective view of an adsorbent bed 200 according to some implementations. Here, the illustrative adsorbent bed 200 has an annular adsorbent ring 205. The adsorbent ring 205 is dimensioned to fit along an inner diameter of the housing 105 of the vessel 100 of FIG. 1.

Within the adsorbent ring 205 is a plurality of adsorbent rods 215. The adsorbent rods 215 run substantially along the length of the adsorbent bed 200. This means that the rods 215 run essentially from the first end 102 to the second end 104 of the vessel 100. Flow channels 210 are provided between the adsorbent rods 215.

The adsorbent ring 205 and the adsorbent rods 215 are fabricated from a material that preferentially adsorbs an undesirable gas. The undesirable gas may be $CO_2$, $H_2S$, mercaptans, heavy hydrocarbons in gaseous phase, or combinations thereof.

The adsorbent material is preferably selected from the 8-ring zeolites having a Si:Al ratio from about 1:1 to about 1000:1, or preferably from about 10:1 to about 500:1, or more preferably from about 50:1 to about 300:1. The term "Si:Al ratio" as used herein means the molar ratio of silica to alumina of the zeolite structure. The more preferred 8-ring zeolites for the capture of sour gas include DDR, Sigma-1 and ZSM-58. Zeolite material having appropriate pore sizes for the removal of heavy hydrocarbons include MFI, faujasite, MCM-41, and Beta. It is preferred that the Si:Al ratio of zeolites utilized for heavy hydrocarbon removal be from about 20:1 to about 1,000:1, and preferably from about 200:1 to about 1,000:1 in order to prevent excessive fouling of the adsorbent.

Where a dehydrated Feed Stream contains hydrogen sulfide, it may be advantageous to formulate the adsorbent with stannosilicates. Specifically, 8-ring zeolites may be fabricated with stannosilicates. The kinetic selectivity of this class of 8-ring materials allows $H_2S$ to be rapidly transmitted into zeolite crystals while hindering the transport of methane. This enhances the selective separation of $H_2S$ from a mixture of $H_2S$ and methane.

The zeolite may be present in the adsorbent ring 205 and the adsorbent rods 215 in any suitable form. For example, zeolite material may be in the form of beads that are packed to form the adsorbent material. Adsorbent beads, or aggregates, for swing adsorption processes are known in the art and can be of any suitable shape, including spherical or irregular. Adsorbent aggregates may be formed by adhering micro-porous zeolite crystals together with binder materials. The micro-pores exist due to the crystalline structure of the zeolite, in this case, preferably 8-ring zeolites. The binder material is typically a dense material that does not have adsorptive properties, but which is used to bind the zeolite crystals. In order to function effectively, the size of binder particles must be smaller than the size of the individual zeolite crystals.

During the pressure swing adsorption process, a Feed Stream "1" will be injected into the contactor 100 and will be passed across the adsorbent material. Preferably, the adsorbent material is an 8-ring zeolite material. The 8-ring zeolites allow $CO_2$ (or other sour gas component) to access the internal pore structure through 8-ring windows in a manner such that the ratio of single component diffusion coefficients of $CO_2$ and methane (i.e., $D_{CO2}/D_{CH4}$) is greater than 5, preferably greater than about 10, and more preferably greater than about 50, and even more preferably greater than 100. Where the Feed Stream contains $H_2S$, 8-ring zeolites allow $H_2S$ to access the internal pore structure through 8-ring windows in a manner such that the ratio of single component diffusion coefficients of $H_2S$ and methane (i.e., $D_{H2S}/D_{CH4}$) is greater than 5, preferably greater than about 20, and more preferably greater than about 50, and even more preferably greater than 100.

Single component diffusion coefficients are taken to be transport diffusion coefficients measured for a pure gas in the Henry's law regime of the adsorption isotherm. The loading of molecules in the zeolite is low in the Henry's law regime and in this regime the Fickian and Stephan-Maxwell diffusion coefficients are nearly equal. The mathematics supporting the analysis of diffusion coefficients is described more fully below.

In some implementations of the adsorbent bed 200, a magnetic material may be incorporated into the adsorbent rods 215. For example, each rod 215 may have an inner bore, and a magnetic material may be placed along the inner bore. The rods 215 may then be subjected to a magnetic or an electromagnetic field during packing. The magnetic field causes the rods 215 to repel one another, thereby assuring uniform spacing between the rods 215. Uniform packing of rods 215 is particularly important for kinetic and fast cycled adsorption processes so that gas components are not preferentially driven through one flow channel 210 over another.

In one aspect, a magnetic or electromagnetic field is applied during each adsorbent loading cycle. This aids in the separation of the rods 215. Application of the magnetic field may further provide for a homogeneous orientation of the zeolite material. Optionally, the magnetic field may be applied during the cycles themselves.

Referring again to FIG. 2A, within the annular adsorbent ring 205 and between the adsorbent rods 215 is a plurality of flow channels. The flow channels are seen at 210. The flow channels 210 define major flow channels that flow along a major axis of the adsorbent bed 200.

The flow channels 210 create a type of structured adsorbent contactor referred to as a "parallel channel contactor." Parallel channel contactors are a subset of adsorbent contactors comprising structured (engineered) adsorbents in which substantially parallel flow channels are incorporated into the adsorbent structure. The flow channels 210 may be formed by a variety of means, some of which are described in U.S. Pat. Publ. No. 2008/0282887 titled "Removal of $CO_2$, $N_2$, and $H_2S$ from Gas Mixtures Containing Same," previously incorporated herein by reference.

The adsorbent material forming the annular ring 205 and the rods 215 has a "kinetic selectivity" for two or more gas components. As used herein, the term "kinetic selectivity" is defined as the ratio of single component diffusion coefficients, D (in $m^2$/sec), for two different species. The single component diffusion coefficients are also known as the Stefan-Maxwell transport diffusion coefficients that are measured for a given adsorbent for a given pure gas component. Therefore, for example, the kinetic selectivity for a particular adsorbent for a component A with respect to a component B would be equal to $D_A/D_B$.

The single component diffusion coefficients for a material can be determined by tests known in the adsorptive materials art. The preferred way to measure the kinetic diffusion coefficient is with a frequency response technique described by Reyes, et al. in "Frequency Modulation Methods for Diffusion and Adsorption Measurements in Porous Solids," J. Phys. Chem. B. 101, pages 614-622 (1997), which is incorporated herein by reference. In the kinetically controlled separation for the vessel 100, it is preferred that kinetic selectivity (i.e., $D_A/D_B$) of the selected adsorbent for the first component (e.g., $CO_2$) with respect to the second component (e.g., methane) be greater than 5.

The term "selectivity" as used herein is based on a binary comparison of the molar concentration of components in the feed stream and the total number of moles of these components adsorbed by the particular adsorbent during the adsorption step of the process cycle under the specific system operating conditions and feed stream composition. For a feed containing a component A, a component B, and optionally additional components, an adsorbent that has a greater "selectivity" for component A than component B will have at the end of the adsorption step of the swing adsorption process cycle a ratio:

$U_A$=(total moles of $A$ in the adsorbent)/(molar concentration of $A$ in the feed)

that is greater than the ratio:

$U_B$=(total moles of $B$ in the adsorbent)/(molar concentration of $B$ in the feed)

where: $U_A$ is the "Adsorption Uptake of component A," and $U_B$ is the "Adsorption Uptake of component B."

Therefore, for an adsorbent having a selectivity for component A over component B that is greater than one:

Selectivity=$U_A/U_B$ (where $U_A > U_B$).

Amongst a comparison of different components in a natural gas feed stream, the component with the smallest ratio of the total moles picked up in the adsorbent to its molar concentration in the feed stream is the lightest component in the swing adsorption process. The light component is taken to be the species, or molecular component, that is not preferentially taken up by the adsorbent in the adsorption process. This means that the molar concentration of the lightest component in the stream coming out during the adsorption step is greater than the molar concentration of that lightest component in the feed stream. In the present disclosure, the adsorbent contactor 100 has a selectivity for a first component (e.g., $CO_2$) over a second component (e.g., methane) of at least 5, more preferably a selectivity for a first component over a second component of at least 10, and most preferably a selectivity for a first component over a second component of at least 25.

Note that it is possible to remove two or more contaminants simultaneously; however, for convenience the component or components that are to be removed by selective adsorption will mostly be referred to herein as a single contaminant or a heavy component.

Recovery of the light component may also be characterized by relative flow rate. Thus, recovery of methane may be defined as the time averaged molar flow rate of the methane in the product stream (shown at $O_1$ in the first outlet 130) divided by the time averaged molar flow rate of the methane in the feed stream (depicted as gas inlet 110). Similarly, recovery of the carbon dioxide and other heavy components is defined as the time averaged molar flow rate of the heavy components in the contaminant stream (shown at $O_2$ in the second gas outlet 120) divided by the time averaged molar flow rate of the heavy component in the feed stream (depicted as gas inlet 110).

In order to enhance the efficiency of the gas separation process, it is proposed herein to provide minor flow channels in the vessel 100. The minor flow channels increase the surface area exposure of the adsorbent material along the rods 215.

Figure 2B:
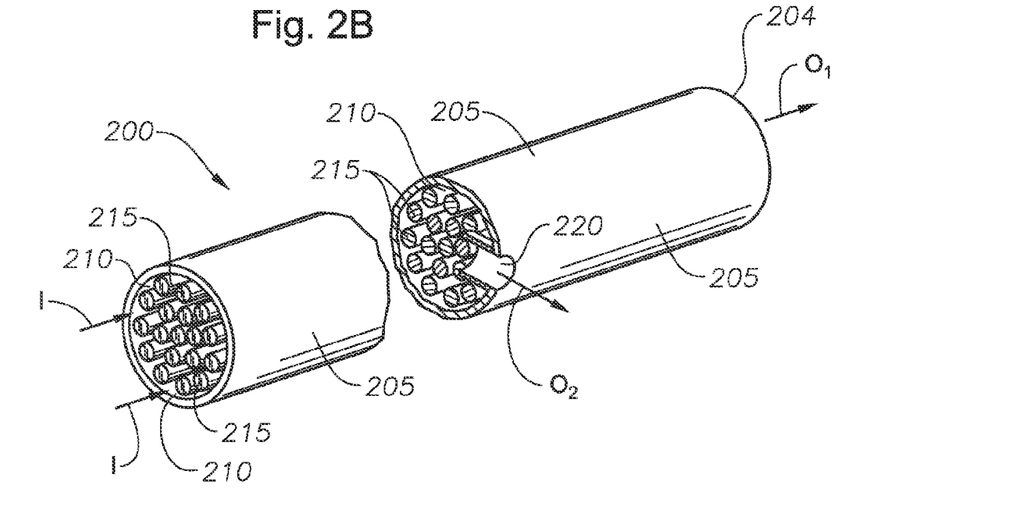
FIG. 2B provides an exposed view of the optional second gas outlet. A transverse flow channel is shown extending into the vessel, serving as a minor flow channel.

FIG. 2B provides an exploded view of the adsorbent bed 200 of FIG. 2A. The adsorbent bed 200 is cut across the optional second gas outlet 120. The major flow channels 210 running through the adsorbent bed 200 are again seen. In addition, a transverse flow channel is seen at 220. The transverse flow channel 220 serves as a minor flow channel. The flow channel 220 is seen partially extending into the adsorbent bed 200. However, the transverse flow channel 220 may optionally extend most of the way around the circumference of the annular adsorbent ring 205.

In the arrangement of FIG. 2B, only a single minor flow channel 220 is shown. However, the adsorbent bed 200 may have a plurality of minor flow channels 220. These may optionally be manifolded together with flow converging on the second gas outlet 120.

Figure 2C:
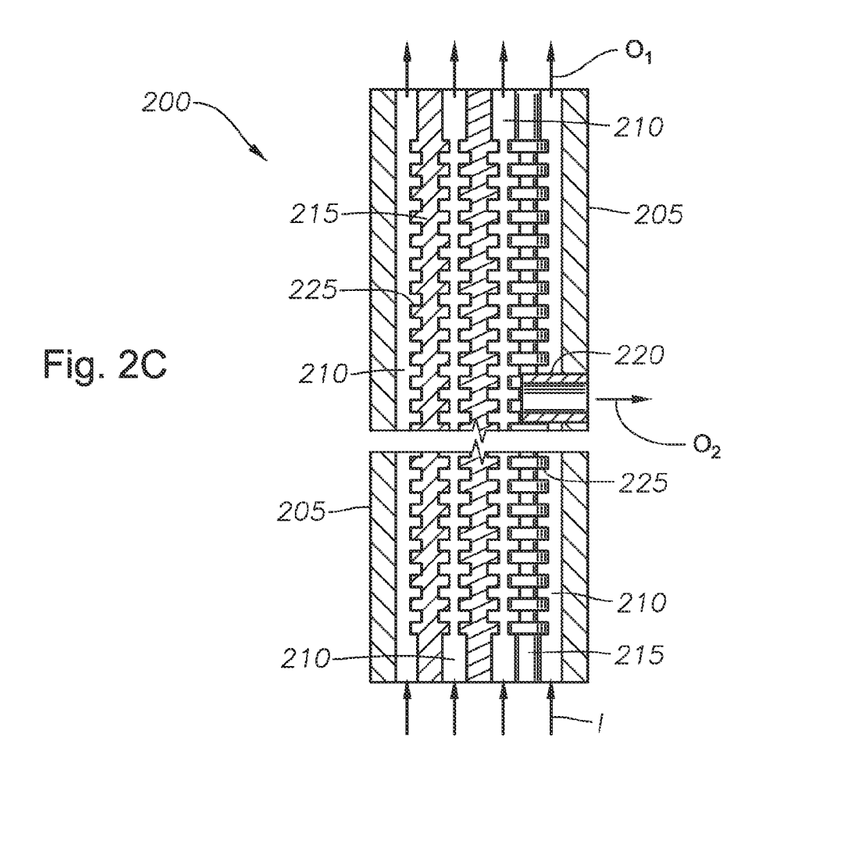
FIG. 2C is a longitudinal cross-sectional view of the adsorbent bed of FIG. 2A. The view is taken across line C-C of FIG. 2A. Here, a series of stepped surfaces are seen along the adsorbent rods, which serve as minor flow channels.

FIG. 2C is a longitudinal cross-sectional view of the adsorbent bed 200 of FIG. 2A. The view is cut through line C-C of FIG. 2A. Longitudinal adsorbent rods 215 are seen in FIG. 2C. In addition, major flow channels 210 are visible between the rods 215.

A series of stepped surfaces 225 are seen along the adsorbent rods 215. The stepped surfaces 225 also serve as minor flow channels. In lieu of stepped surfaces 225, the surfaces 225 may be helical or spiraled surfaces. In any arrangement, the stepped surfaces 225 may be used in addition to or in lieu of the transverse channel 220 to increase surface area and improve kinetic selectivity without need of large and expensive heat transfer units.

The major 210 and minor 220, 225 flow channels provide paths in the contactor 200 through which gas may flow. Generally, the flow channels 210, 220, 225 provide for relatively low fluid resistance coupled with relatively high surface area. Flow channel length should be sufficient to provide the desired mass transfer zone, which is, at least, a function of the fluid velocity and the ratio of surface area to channel volume.

The flow channels 210, 220, 225 are preferably configured to minimize pressure drop in the vessel 100. Thus, tortuous flow paths are minimized or avoided. If too much pressure drop occurs across the bed 200, then higher cycle frequencies, such as on the order of greater than 100 cpm, are not readily achieved. In addition, it is preferred that the rods 215 be equidistantly spaced so as to create a degree of channel uniformity.

In one aspect, the flow channels 210 are generally divided so that there is little or no cross-flow. In this instance, a fluid flow fraction entering a channel 210 at the first end 102 of the contactor 100 does not significantly communicate with any other fluid fraction entering another channel 210 at the first end 102 until the fractions recombine upon exiting at the second end 104. In this arrangement, the volumes of the major flow channels 210 will be substantially equal to ensure that substantially all of the channels 210 are being fully utilized, and that the mass transfer zone defined by the interior volume of the contactor vessel 100 is substantially equally contained.

The dimensions of the flow channels 210 can be computed from considerations of pressure drop along the contactor vessel 100. It is preferred that the flow channels 210 have a channel gap from about 5 to about 1,000 microns, preferably from about 50 to about 250 microns. As utilized herein, the "channel gap" of a flow channel 210 is defined as the length of a line across the minimum dimension of the flow channel 210 as viewed orthogonal to the flow path. For instance, if the flow channel 210 is circular in cross-section, then the channel gap is the internal diameter of the circle. However, if the channel gap is rectangular in cross-section, the flow gap is the distance of a line perpendicular to and connecting the two longest sides of the rectangular (i.e., the length of the smallest side of the rectangle).

It should be noted that the major flow channels 210 can be of any cross-sectional configuration or geometric profile. In FIGS. 2A and 2B, the major flow channels 210 are star-shaped. Regardless of the shape, it is preferred that the ratio of the volume of adsorbent material to the flow channel volume in the adsorbent contactor 100 be from about 0.5:1 to about 100:1, and more preferably from about 1:1 to about 50:1.

In some pressure swing applications, particularly with RCPSA applications, the flow channels are formed when adsorbent sheets are laminated together. The flow channels within the sheets will contain a spacer or mesh that acts as a spacer. However, the spacers take up much-needed space. Therefore, laminated sheets are not desirable in the present contactor 100 and associated processes.

Figure 3:
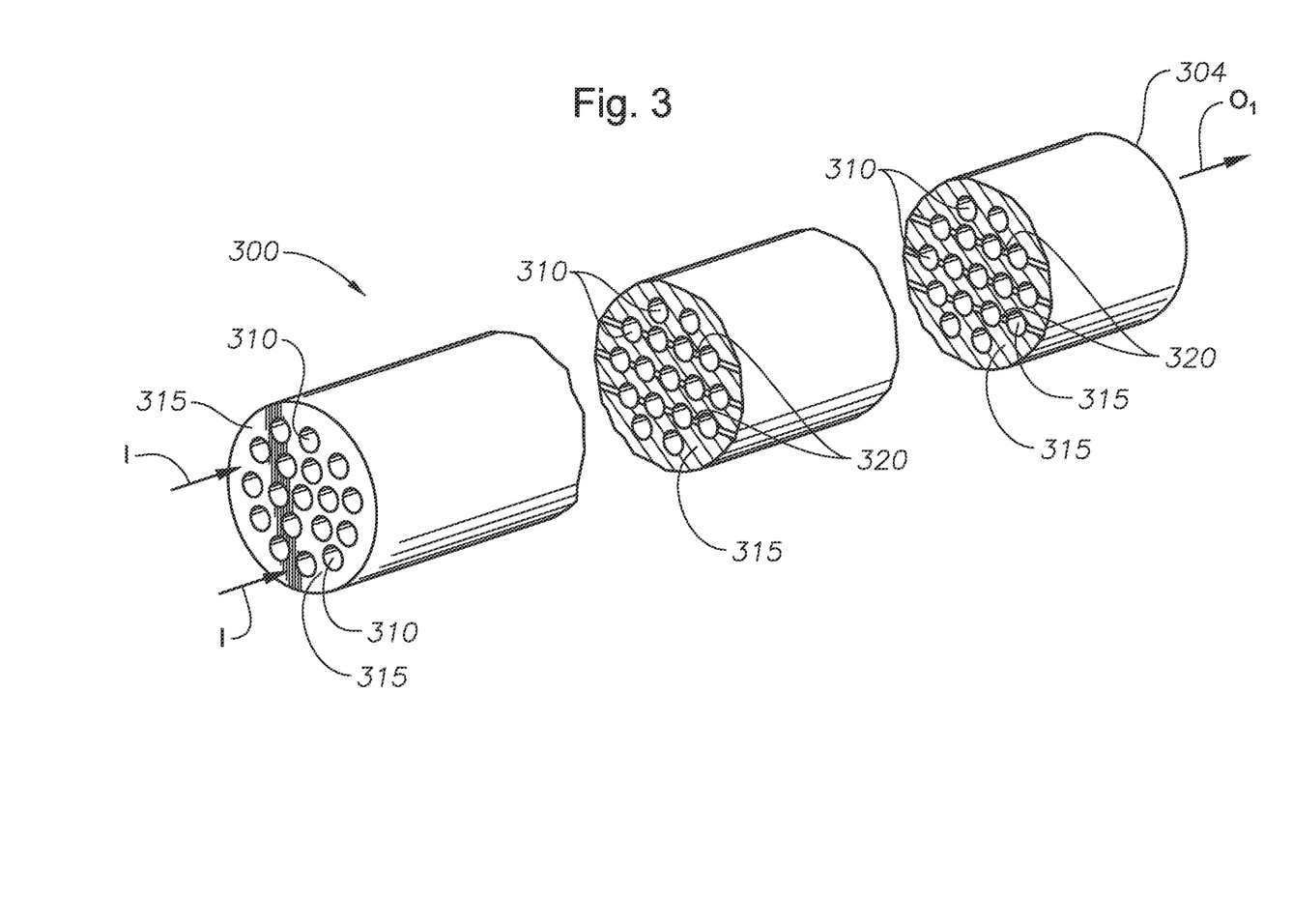
FIG. 3 is a perspective view of an adsorbent bed and flow channels for the pressure swing adsorption vessel of FIG. 1. Major flow channels are seen between adsorbent rods along a major axis of the adsorbent bed. Transverse flow channels are seen in exploded-away portions of the adsorbent bed, which serve as minor flow channels.

In lieu of laminated sheets, a plurality of small, transverse minor flow channels may be machined through the adsorbent rods. FIG. 3 provides a perspective view of an adsorbent bed 300 for the pressure swing adsorption vessel of FIG. 1, in a modified arrangement. The adsorbent bed 300 has an outer surface 305. The outer surface 305 is dimensioned to fit along an inner diameter of the housing 105 of the vessel 100 of FIG. 1.

Major flow channels 310 are provided within a monolithic adsorbent material 315. The major flow channels 310 are formed along a major axis of the adsorbent bed 300. However, to further increase surface area along the adsorbent rods, small transverse channels 320 are formed through the monolithic material 315. These channels serve as minor flow channels 320.

The minor flow channels 320 may be very small tubular channels, having a diameter of less than about 25 microns, for example. The minor flow channels 320 are not so large as to completely sever an adsorbent rod 315. In this way, the need for supporting spacers is avoided.

The minor flow channels 320 facilitate pressure balancing between the major flow channels 310. Both productivity and gas purity may suffer if there is excessive channel inconsistency. In this respect, if one flow channel is larger than an adjacent flow channel or receives more gas stream than another, premature product break-through may occur. This, in turn, leads to a reduction in the purity of the product gas to unacceptable purity levels. Moreover, devices operating at cycle frequencies greater than about 50 cycles per minute (cpm) require greater flow channel uniformity and less pressure drop than those operating at lower cycles per minute.

Returning now to FIGS. 1 and 2, the vessel 100 in FIG. 1 is shown as a cylinder, and the adsorbent rods 215 therein are shown as tubular members. However, other shapes may be employed that are suitable for use in swing adsorption process equipment. Non-limiting examples of vessel arrangements include various shaped monoliths having a plurality of substantially parallel channels extending from one end of the monolith to the other; a plurality of tubular members; stacked layers of adsorbent sheets with spacers between each sheet; multi-layered spiral rolls or bundles of hollow fibers, as well as bundles of substantially parallel solid fibers.

Figure 4:
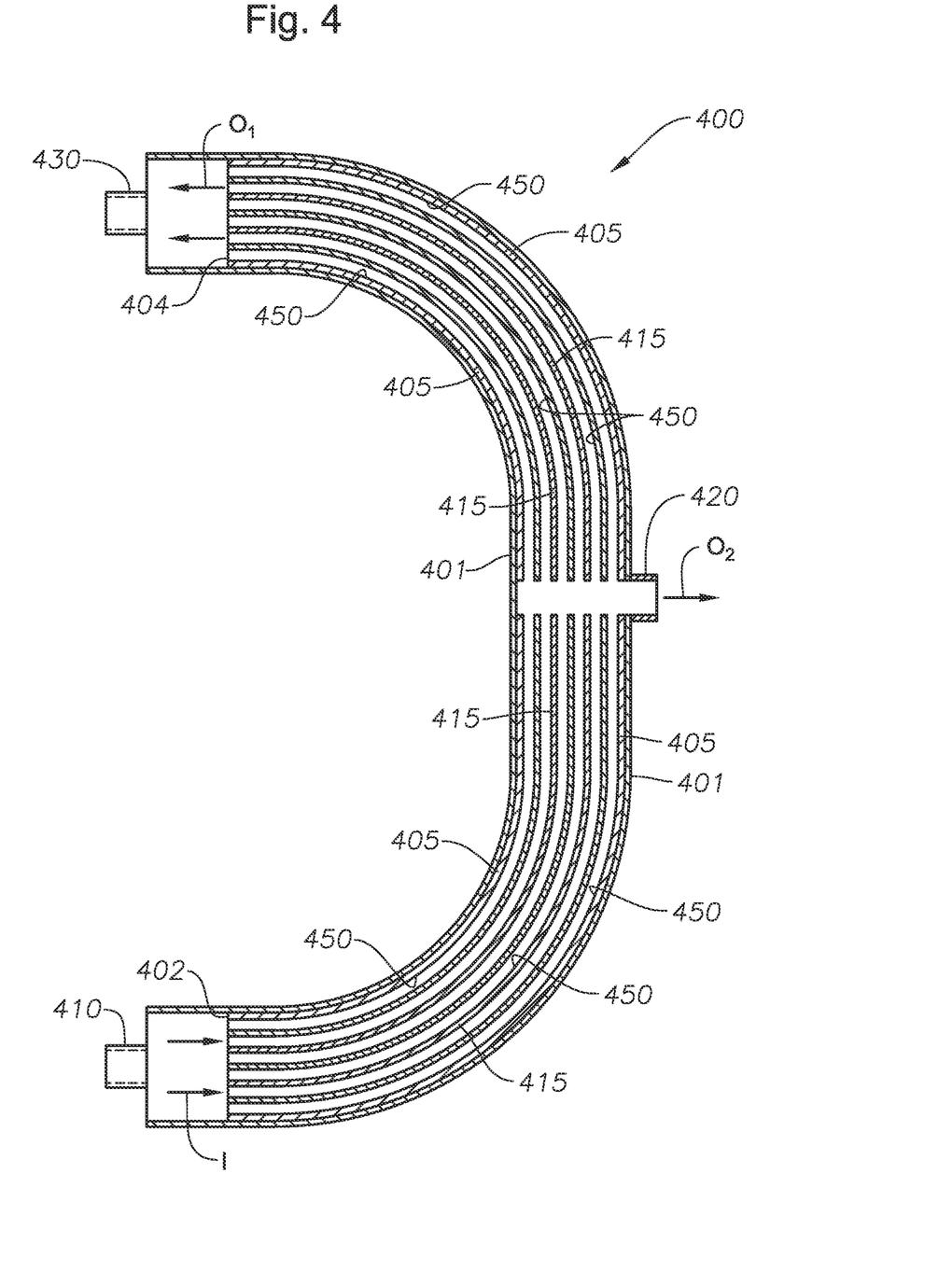
FIG. 4 is a cross-sectional view of an adsorbent bed and flow channels for the pressure swing adsorption vessel of FIG. 1. Major flow channels are again seen between adsorbent rods along a major axis of the adsorbent bed. Here, the major axis is curvilinear.

FIG. 4 is a cross-sectional view of a pressure swing adsorption vessel 400, in an alternate arrangement. In this arrangement, the vessel 400 is semi-circular. The vessel 400 again defines an elongated, pressure-containing body. The vessel 400 includes a housing 401. Preferably, the housing 401 is fabricated from iron or steel.

The vessel 400 has a first end shown at 402, and a second end shown at 404. A gas inlet 410 is provided at the first end 402, while a first gas outlet 430 is provided at the second end 404. Optionally, a second gas outlet 420 is provided intermediate the first end 402 and the second end 404, or intermediate the gas inlet 410 and the first gas outlet 430.

A plurality of adsorbent rods 415 are provided along a major axis of the vessel 400. Stated another way, the rods 415 (or fibers) conform to the curvilinear shape of the vessel 400. Preferably, an adsorbent ring 405 is also provided within the vessel 400 and along an inner surface thereof. Between the adsorbent rods 415 are major flow channels 450. A dehydrated raw gas stream flows through the major flow channels 450 for gas separation.

In FIG. 4, five adsorbent rods 415 are shown; however, it is understood that the vessel 400 will contain tens or even hundreds or even several thousands of small rods 415. The major flow channels 450 between the rods 415 are preferably 50 to 100 microns in diameter.

It will be appreciated that with the arrangement of FIG. 4, separate parallel manifolds of ports for interfacing with a valving interface (such as a rotary or a non-rotary valving interface) can be arranged on both sides of the multiplicity of adsorbent holders, thus enabling a cycle to be delivered to the adsorbent material without using empty connecting tubes which generate dead volumes. It is also understood that the location of the flow channels 450 and the rods 415 may be reversed, as demonstrated in FIG. 3.

In the vessel 400 of FIG. 4, minor flow channels are also provided. Those may be in accordance with transverse channel 220 of FIG. 2B, stepped (or spiraled) surfaces 225 of FIG. 2C, or both. In either of these arrangements, the adsorbent material may be coated onto the vessel 200/400 and the rods 215/415. Alternatively, the rods 215/415 may be formed directly from the adsorbent material with a suitable binder. An example of a geometric shape formed directly from the adsorbent plus binder would be the extrusion of a zeolite/polymer composite into a monolith. Another example of a geometric shape formed directly from the adsorbent would be extruded or spun hollow fibers made from a zeolite/polymer composite.

In the preferred pressure swing adsorption process, the gaseous mixture is passed over a first adsorption bed in a first vessel. A light component-enriched product stream emerges from the bed depleted, while the contaminant, or heavy component, remains adsorbed in the bed. After a predetermined time or, alternatively when a break-through of the contaminant or heavy component is observed, the flow of the gaseous mixture is switched to a second adsorption bed in a second vessel for the purification to continue. While the second bed is in adsorption service, the sorbed contaminant, or heavy component is removed from the first adsorption bed by a reduction in pressure. In some embodiments, the reduction in pressure is accompanied by a reverse flow of gas to assist in desorbing the heavy component. As the pressure in the vessels is reduced, the heavy component previously adsorbed in the bed is progressively desorbed to a heavy component enriched product stream. When desorption is complete, the sorbent bed may be purged with an inert gas stream such as nitrogen or a purified stream of process gas.

After the first bed has been regenerated so that it is again ready for adsorption service, the flow of the gaseous mixture is switched from the second bed to the first bed, and the second bed is regenerated. The total cycle time is the length of time from when the gaseous mixture is first conducted to the first bed in a first cycle to the time when the gaseous mixture is first conducted to the first bed in the immediately succeeding cycle, i.e., after a single regeneration of the first bed. The use of third, fourth, fifth, etc. vessels in addition to the second vessel can serve to increase cycle time when the adsorption cycle time for the bed is shorter than the cycle times for the desorption and purging cycles for the bed.

To illustrate the use of the contactor vessel 100, examples are presented based on a model of the kinetic rapid cycle pressure swing adsorption (RCPSA) process. This model is called the Continuous Countercurrent Steady State (CCS). In the examples, a feed stream containing hydrogen, methane, and carbon dioxide is introduced into a virtual vessel. Two separate product streams are then released—one representing a Product Stream (1) after adsorbent loading, and another representing a Product Stream (2) after purging or blowdown.

The CCS model allows for the calculation of the composition of the separated Product Streams leaving an RCPSA unit when the process has reached its periodic steady states. The CCS representation relies on the observation that at a periodic state, the RCPSA produces a constant composition (i.e. purity) of products. Over any individual cycle, the loading (i.e. adsorbed material) on the adsorbent bed oscillates between two fixed extremes for the Product Streams. The CCS simulation calculates the periodic state axial profiles and product compositions, as the solution of simultaneous differential equations. The model has been discussed in technical literature, such as in M. Suzuki, AIChE Symposium Ser. 81 (242) p. 67, (1985); and Farooq and Ruthven, AIChE J., 36 (2) p. 310, (1990).

Using this approach, examples of component gas separations are demonstrated:

Example 1

A kinetic separation using non-thermal swing PSA (i.e., no thermal step) is first shown in Table 1. The separation provides for the recovery of $CO_2$ and $CH_4$ at high purity from a Feed Stream containing $CO_2$, $CH_4$ and $H_2$.

In this separation, the Feed Stream contains by volume 25% $CO_2$, 72% $CH_4$, and a remaining 3.0% $H_2$. The components are separated by a kinetic separation on an adsorbent material such as the Takeda 3A carbon molecular sieve. During adsorption, carbon dioxide is adsorbed onto the mol. sieve, while methane and hydrogen are released as a first product.

As can be seen in Table 1, the first product, indicated at Product Stream (1), contains 95.08% $CH_4$. This represents a high purity stream. The second product, indicated at Production Stream (2), is recovered during a purge cycle. Product Stream (2) contains 99.76 vol. % $CO_2$. This also represents a high purity stream.

TABLE 1

| mol % | Feed Stream | Product Stream (1) | Product Stream (2) |
|---|---|---|---|
| $H_2$ | 3.0 | 3.96 | 0.00 |
| $CH_4$ | 72.0 | 95.08 | 0.24 |
| $CO_2$ | 25.0 | 0.95 | 99.76 |

Example of Kinetic RCPSA Fractionation with High Purity Products

The purities and recoveries demonstrated in Table 1 are comparable to those purportedly achieved by Urano, et al., as published in EP 0 426 937 in 1991. This European patent was obtained together by Saibo Gas Co., Ltd. and Mitsubishi Petrochemical Engineering Co., Ltd. Urano, et al. claimed the following separation:

TABLE 2

| mol % | Feed Stream | Product Stream (1) | Product Stream (2) |
|---|---|---|---|
| $H_2$ | 2.7 | 3.61 | 0.00 |
| $CH_4$ | 72.1 | 96.05 | 1.03 |
| $CO_2$ | 25.2 | 0.34 | 98.97 |

EP 0 426 937

However, Urano, et al., relied upon a thermal step. In contrast, the current process, using fast cycle kinetics, is able to provide substantially the same separation without using a thermal swing during regeneration. Accordingly there is no need for a heat exchanger and associated equipment as required by Urano, et al. The current process is able to take advantage of higher mass transfer and kinetic cycling with less equipment.

Example 2

A second example of gas component separation is also provided herein. In this additional example, a kinetic separation using non-thermal swing PSA (i.e., no thermal step) is again provided, with results shown in Table 3. The separation provides for the recovery of $CO_2$ and $CH_4$ at high purity from a Feed Stream containing $CO_2$, $CH_4$ and $H_2$.

In this separation, the Feed Stream contains by volume 50.0% $CO_2$, 48.5% $CH_4$, and a remaining 1.5% $H_2$. It is noted here that the Feed Stream in this Example 2 contains twice the relative amount of CO2 as compared to Example 1. The components are again separated by a kinetic separation on an adsorbent material such as the Takeda 3A carbon molecular sieve. During adsorption, carbon dioxide is adsorbed onto the mol. sieve, while methane and hydrogen are released as a first product.

The first product, indicated at Product Stream (1), contains 96.04% $CH_4$. This represents a high purity stream. The second product, indicated at Production Stream (2), is recovered during a purge cycle. As shown in Table 2, Product Stream (2) contains 99.95 vol. % $CO_2$. This represents a very high purity stream.

Once again, the purities in Table 3 are similar to those achieved by Urano, et al., shown in Table 2. However, the disclosed process, using fast cycle kinetics, is able to provide the same separation without using the thermal step and the associated equipment that is required by Urano et al.

TABLE 3

| mol % | Feed Stream | Product Stream (1) | Product Stream (2) |
|---|---|---|---|
| $H_2$ | 1.5 | 2.97 | 0.00 |
| $CH_4$ | 48.5 | 96.04 | 0.05 |
| $CO_2$ | 50.0 | 0.99 | 99.95 |

Example of Kinetic RCPSA Fractionation with Multiple High Purity Products

A separate model may also be used for predicting component separation and for designing a PSA contactor. This model relies upon an adsorption isotherm. In this respect, for a well-designed kinetically controlled swing adsorption processes, the amount of heavy component in the micro-pores of an adsorptive material can be approximately computed from the adsorption isotherm of the heavy component in equilibrium with its local gas phase concentration in the contactor. Similarly, for a well-designed equilibrium controlled swing adsorption process, the amount of heavy component in the micro-pores can be approximately computed from the competitive adsorption isotherm of the heavy and light components in equilibrium with their local gas phase concentration in the contactor. These approximations are possible because, in well-designed swing adsorption processes, the contactor provides good mass transfer characteristics between the gas phase and the adsorbed phase in the micro-pores of the contactor.

The maximum attainable loading of the heavy component in the macro-pores or free volume of the contactor is called $q_s$ (units for $q_s$ are milli-mole/m³ of the micro-porous or polymeric material). At low pressures, the adsorption isotherm for the heavy component usually obeys Henry's Law. Therefore, the amount of heavy component adsorbed in the micro-porous or polymeric material may be presented as:

$$q_{Heavy} = K_{Heavy} P_{Heavy} q_s \text{ (in milli-mole/m}_3\text{)}$$

where $K_{Heavy}$ is the Henry's constant, and
$P_{Heavy}$ is the partial pressure of the heavy component.
The Henry's constant ($K_{Heavy}$) depends on temperature, and usually varies according to the equation:

$$K_{Heavy} = K_0 e^{\frac{\Delta H}{RT}} \text{(in pascals}^{-1}\text{)}$$

where $K_0$ is a pre-exponential, and
$\Delta H$ is the heat of adsorption (in joule/mole).

To improve selectivity and recovery for a kinetically controlled swing adsorption process, the inlet temperature and pressure should be chosen such that at the end of the adsorption step, the loading of the heavy component in the micro-pores near the point at which the feed stream is introduced to the contactor should be greater than 0.15 $q_s$ and preferably greater than 0.3 $q_s$ and even more preferably greater than 0.6 $q_s$. This requirement places a lower bound on the inlet pressure and a maximum bound on the inlet temperature. With increasing loading of the heavy component in the micro-pores of the adsorbent, the amount of material that is selectively adsorbed in the contactor is increased and the amount of material that can be selectively released in the desorption step is increased. Increasing the loading significantly beyond this range reduces the recovery of the light component because the slope of the adsorption isotherm tends to decrease with increasing pressure.

To maximize the recovery of the light component, it is also preferred that near the point at which the Feed Stream is introduced to the contactor, the slope of the adsorption isotherm for the heavy component is large enough so that:

$$\frac{\partial q_{Heavy}}{\partial P_{Heavy}} > \alpha K_{Heavy} q_s$$

where $\alpha=\frac{1}{50}$, or more preferably $\alpha=\frac{1}{25}$, or even more preferably $\alpha=\frac{1}{8}$.

This inequality places a maximum bound on the inlet pressure and a minimum bound on the inlet temperature. As such, these requirements define a window (i.e., maxima and minima) for Feed Stream pressure and temperature in which the recovery of the light component is optimized. This window is important in natural gas separations because some natural gas is usually produced at pressures ranging from 1,500 to 7,000 psi. These feed pressures are usually too high to fall within the optimum recovery window for methane, which acts as a light component in a swing adsorption separation.

It is noted here that an effective diffusivity ratio, or selectivity, may be expressed in a manner which takes into account both intrinsic diffusivity and the slope of the equilibrium isotherm. The slope of the equilibrium isotherm is:

$$\frac{\Delta q}{\Delta c}$$

where: Δq is the change in loading of a component; and
Δc is the change in concentration of that component.
This slope is identical to the Henry constant at low component concentrations.

The effective diffusivity ratio (or selectivity of species 1 by the adsorbent in preference to species 2 where species 1 is the "Heavy,"—e.g. $CO_2$ and species 2 is the "Light," e.g., $CH_4$, can be derived with the following result:

$$\frac{D1}{D2} \times \left(\frac{Slope2}{Slope1}\right)^2$$

where:
D1 is the diffusivity of the Heavy species;
D2 is the diffusivity of the Light species;

$$\frac{D1}{D2}$$

is an intrinsic diffusivity ratio measuring the difference in uptake rates for kinetic adsorbents of interest. This value may be on the order of 100 to 500, and possibly much higher.
Slope2 is the change in concentration of the Light species.
Slope1 is the change in concentration of the Heavy species.
A conservative value of the ratio of slopes $$\left(\frac{Slope2}{Slope1}\right)$$

(using a typical Henry region), is of the order of 0.3 for the kinetic adsorbents of interest. Therefore selectivity is of the order of 100×0.3×0.3=9. It is noted that if the Light species becomes even less prone to be adsorbed (i.e. Slope2 reduces), its D2 value also decreases to reflect the lowered uptake.

It is possible to access the optimum light component recovery window for most heavy component (such as $CO_2$, $N_2$, and $H_2S$) separations by preconditioning the natural gas with a turbo-expander. The turbo-expander recovers the energy from the gas expansion. Energy recovered from gas expansion can then be used for power generation or to help recompress separated acid gas components (such as $CO_2$ or $H_2S$) so that they can be disposed of in underground formations. Underground formations that are suitable for disposal/sequestration of $CO_2$ and $H_2S$ include aquifers that have a top seal that prevents significant loss of injected acid gas components, oil reservoirs, gas reservoirs, depleted oil reservoirs and depleted gas reservoirs.

Typically, the separated $CO_2$ and $H_2S$ must be recompressed to pressures greater than 2,000 psi, and often to pressures greater than 5,000 psi, for acid gas injection. Thus, it is helpful to be able to reuse energy recovered from a turbo-expander for recompression. The cost of a turbo-expander is less than a gas fired turbine producing the same amount of power. As such, it is economically advantageous to use a turbo-expander to capture energy from gas expansion used to condition natural gas for the optimum methane recovery window. The energy can either be recovered with a shaft-coupled electric generator, or with a shaft-coupled compressor.

Figure 5:
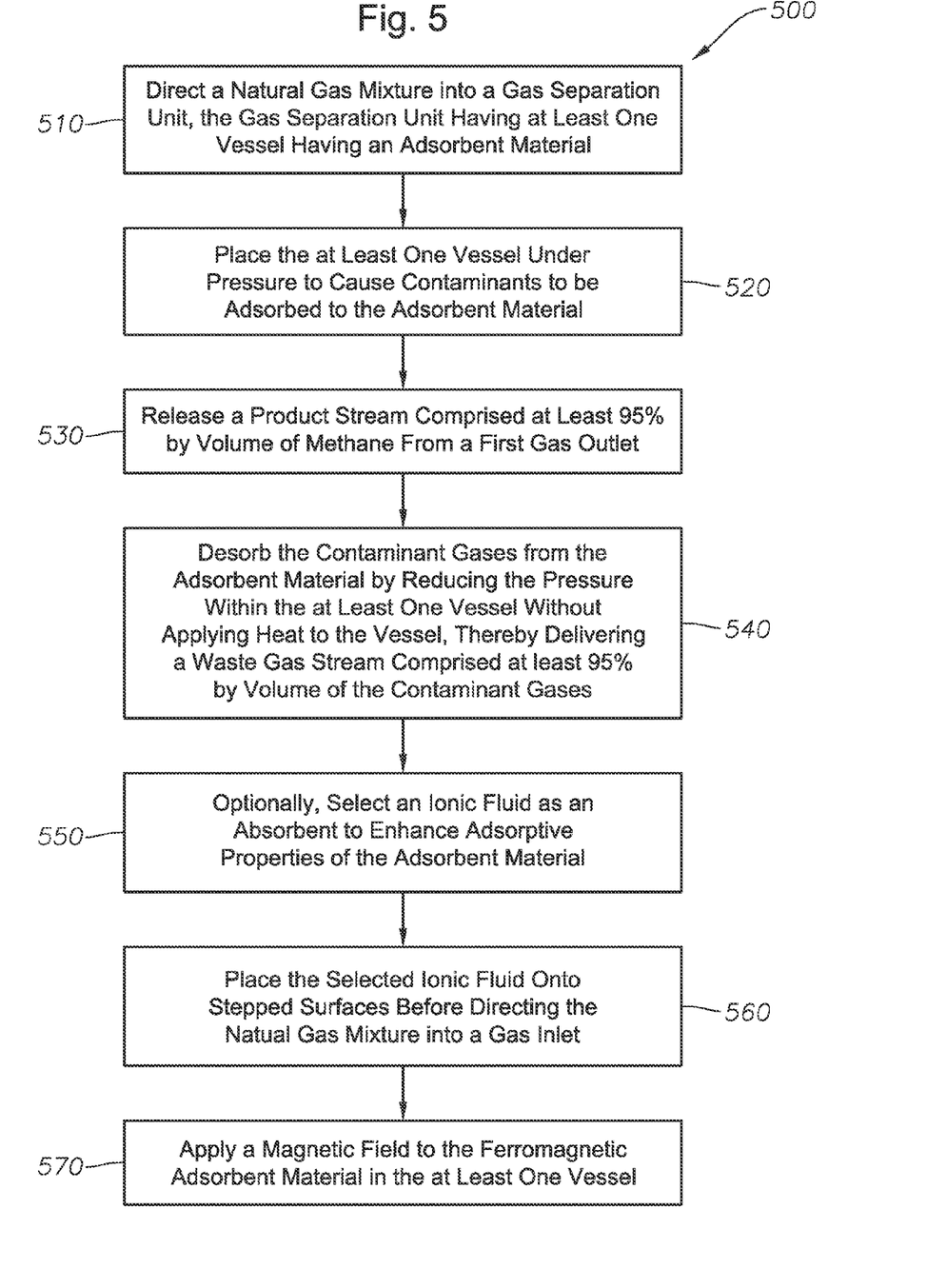
FIG. 5 is a flowchart demonstrating steps of processes for separating methane from a natural gas mixture.

Based on the above-described technology and the improved contacting vessels 100, 600A, and 600B, methods 500 of separating methane from a natural gas mixture are provided herein. FIG. 5 provides a flowchart demonstrating steps for the methods 500 of separating methane from a natural gas mixture. The methods 500 employ pressure swing adsorption in one or more vessels, without thermal heating of the vessel during a purging cycle.

As used in the methods 500, the term pressure swing adsorption includes conventional pressure swing adsorption (PSA), as well as so-called partial pressure swing or displacement purge adsorption (PPSA) technologies. The swing adsorption processes may optionally be conducted with rapid cycles, in which case they are referred to as rapid cycle pressure swing adsorption (RCPSA), and rapid cycle partial pressure swing or displacement purge adsorption (RCPPSA) technologies.

The methods 500 first include directing the natural gas mixture into a gas separation unit. This is provided in Box 510. The gas separation unit includes at least one pressure swing adsorption vessel. The vessel utilizes an adsorbent material having a kinetic selectivity for contaminants over methane that is greater than 5. The contaminants may be $CO_2$, $H_2S$, $H_2O$, heavy hydrocarbons, VOC's, or combinations thereof.

Each vessel has a gas inlet and a first gas outlet. In addition, each vessel has at least two major flow channels through the adsorbent material. The major flow channels place the gas inlet and the first gas outlet in fluid communication.

The vessels are unique in that they also include at least two minor flow channels through the adsorbent material. The minor flow channels are in fluid communication with the major channels. The minor flow channels increase the surface area of the adsorbent material, thereby increasing adsorbence.

In some implementations, each of the at least two major flow channels is formed from and/or along the major axis of a plurality of rods. The rods are spaced substantially equidistantly apart, providing the flow channels with a substantially uniform flow volume. In this embodiment, the at least two minor flow channels may be formed by a plurality of stepped surfaces along the respective rods, or by spiraled surfaces. Alternatively, the at least two minor flow channels is formed by flow channels that intersect the at least two major flow channels and which place the gas inlet and a second gas outlet in fluid communication. Preferably, the at least two minor flow channels are substantially transverse to the at least two major flow channels.

The methods 500 also include placing the at least one vessel under pressure to cause contaminants in the natural gas mixture to be adsorbed onto the adsorbent material. This is seen in Box 520. In accordance with the methods 500, contaminants within the natural gas mixture become kinetically adsorbed in the gas phase within the adsorbent material. The contaminants reside under pressure in the surfaces and micropores of the adsorbent material.

The methods 500 further include releasing a product stream comprised of at least 95% by volume methane from the first gas outlet in the vessel. This is shown at Box 530. While the product stream primarily comprises methane, it may also contain hydrogen, nitrogen, or combinations thereof.

The methods 500 also include desorbing or purging the contaminant gases from the adsorbent material. This is done by reducing the pressure within the vessel. The desorbing step is provided at Box 540. The desorbing step of Box 540 is done without applying heat to the vessel. From the desorbing step of Box 540, a waste gas stream is delivered that comprises at least 95% by volume of the contaminant gas or gases.

Preferably, the sorbing 520 and desorbing 540 steps take place in a combined cycle of less than one minute. In this way, the method 500 provides a rapid cycle pressure swing adsorption process. RCPSA contactors may utilize a rotary valving system to conduct the gas flow through a rotary adsorber module, although non-rotary valving may also be used. The absorber module includes valving elements angularly spaced around a circular path. The rotary adsorber module also normally includes multiple tubes held between two seal plates on either end of the module. The seal plates are in contact with a stator comprised of separate manifolds wherein the inlet gas is conducted to the RCPSA tubes, and processed purified product gas is conducted away from the module. By suitable arrangement of the seal plates and manifolds, a number of individual compartments or tubes may pass through the cycle. More specifically, each tube or compartment is successively passed to a gas flow path in the appropriate direction and pressure to achieve one of the incremental pressure/flow direction steps in the complete RCPSA cycle. The tubes or compartments may either move or be stationary to generate valving.

It is preferred that the methods 500 be conducted using RCPSA. In RCPSA, each of the tubes is successively cycled through the sorption 520 and desorption 540 steps as the rotary module completes a cycle of operation. The cycling process allows the RCPSA technology to have a more efficient use of the adsorbent material. The quantity of adsorbent material required with RCPSA technology may be much less than that required for conventional PSA technology to achieve the same separation quantities and qualities. As a result, the footprint, investment, and the amount of active adsorbent required for RCPSA is typically significantly lower than that for a conventional PSA unit processing an equivalent amount of gas.

Returning to step 540, for desorbing the carbon dioxide (or other contaminant gas) from the adsorbent material, the waste gas stream may be delivered through the gas inlet. Alternatively, valving may be arranged so that the waste gas stream is delivered through the first gas outlet. In one aspect, the at least one adsorbent vessel further comprises a second gas outlet intermediate the gas inlet and the first gas outlet. In this instance, desorbing the contaminant gases per Box 540 may release a first portion of the waste gas stream from the first gas outlet, and a second portion of the waste gas stream from the second gas outlet.

In some implementations of the methods 500, the step 540 of desorbing the contaminant gases comprises releasing a first portion of the waste gas stream during a first time period, and a second portion of the waste gas stream during a second time period. The first portion of the waste gas stream may comprise at least 98% by volume $CO_2$. The second portion of the waste gas stream may comprise primarily nitrogen, hydrogen, methane, $H_2O$, or combinations thereof. It is noted that the specific order of exhausting may be reversed or manipulated.

In some implementations, the methods 500 further include selecting an ionic fluid as an absorbent. This is shown at Box 550. The ionic fluid is used to enhance adsorptive properties of the adsorbent material. The methods 500 then include placing the selected ionic fluid onto surfaces of the adsorbent material along the major and/or minor flow channels before directing the natural gas mixture into the gas inlet. This is provided at Box 560. The ionic liquid may be regarded as a liquid phase version of a cation-exchanged zeolite.

In another aspect, the methods 500 further include applying a magnetic field to the adsorbent material in the vessel. This is shown at Box 570. The magnetic field energizes a ferromagnetic material that may be placed along the adsorbent rods, essentially causing the rods to repel one another. This, in turn, creates uniform flow channels for the feed stream.

By using an adsorbent material forming elongated major flow axes, the present processes are capable of obtaining methane recovery of greater than about 80 vol. %, more preferably greater than about 85 vol. %, even more preferably greater than about 90 vol. %, and most preferably still greater than about 95 vol. %, even when the natural gas is fed at high pressures, such as at inlet pressures greater than about 50 psig, preferably at inlet pressures greater than about 150 psig, more preferably at inlet pressures greater than about 500 psig, even more preferably at inlet pressures greater than about 1,000 psig. Indeed, the present method can be used even when the gas stream is at an exceptionally high pressure of about 3,000 psig.

While it will be apparent that the inventions herein described are well calculated to achieve the benefits and advantages set forth above, it will be appreciated that the inventions are susceptible to modification, variation and change without departing from the spirit thereof.

What is claimed is:

1. A fractionation vessel for separating methane from a natural gas mixture, the vessel comprising:
    a housing;
    a gas inlet for receiving the natural gas mixture into the housing at a pressure of at least 100 psig;
    a first gas outlet for releasing at least a portion of the natural gas mixture from the housing;
    an adsorbent material within the housing, the adsorbent material having a kinetic selectivity for contaminants over methane greater than 5, such that the contaminants become kinetically adsorbed within the adsorbent material in gas phase;
    at least two major flow channels through the adsorbent material, the at least two major flow channels placing the gas inlet and the first gas outlet in fluid communication; and
    at least one minor flow channel through the adsorbent material, the at least one minor channel being in fluid communication with the major channels.

2. The fractionation vessel of claim 1, further comprising:
    a manifold for cycling the natural gas mixture through sequential releasing and desorbing stages in a combined cycle of less than one minute, said manifold comprising valving interfaces.

3. The fractionation vessel of claim 2, wherein the valving interfaces comprise rotary valves, non-rotary valves, or combinations thereof.

4. The fractionation vessel of claim 2, wherein the valving interfaces cooperate with other fractionation vessels to form a pressure swing adsorption system comprising:
    at least one service bed providing adsorption,
    at least one bed in regeneration undergoing pressure reduction, and
    at least one regenerated bed held in reserve for use in the adsorption system when the at least one service bed becomes substantially saturated.

5. The fractionation vessel of claim 1, further comprising:
    a second gas outlet intermediate the gas inlet and the first gas outlet for releasing a portion of a waste gas stream when the vessel is desorbed.

6. The fractionation vessel of claim 5, wherein the second gas outlet is substantially orthogonal to the major flow channels.

7. The fractionation vessel of claim 1, wherein:
the at least one minor flow channel is formed by flow channels that intersect the at least two major flow channels and which place the gas inlet and the second gas outlet in fluid communication.

8. The fractionation vessel of claim 1, wherein:
each of the at least two major flow channels is formed from, and along the major axis of, a plurality of rods; and
the plurality of rods are spaced substantially equi-distantly apart, providing the flow channels with a substantially uniform volume.

9. The fractionation vessel of claim 8, wherein the at least two minor flow channels is formed by a plurality of stepped surfaces along the respective rods, by spiral surfaces along the respective rods, or combinations thereof.

10. The fractionation vessel of claim 8, wherein:
each of the plurality of rods comprises a bore therein; and
each of the plurality of rods comprises a magnetic material placed along the bore.

11. The fractionation vessel of claim 10, wherein the at least one minor flow channel is transverse to the at least two major flow channels.

12. The fractionation vessel of claim 1, wherein the adsorbent material comprises an outer surface at least partially coated with an ionic fluid to enhance adsorptive properties of the adsorbent material.

13. The fractionation vessel of claim 1, wherein the adsorbent material comprises an annular ring along an inner diameter of the vessel.

14. The fractionation vessel of claim 1, wherein the adsorbent material comprises a monolithic body having longitudinal through-openings forming the at least two major flow channels.

* * * * *